(12) United States Patent
Waeger

(10) Patent No.: US 8,905,956 B2
(45) Date of Patent: Dec. 9, 2014

(54) THORACIC LUMBAR SACRAL POSTURE GARMENT DEVICE

(75) Inventor: Robert D. Waeger, Long Beach, CA (US)

(73) Assignee: AlignMed Inc., Santa Ana, CA (US)

( * ) Notice: Subject to any disclaimer, the term of this patent is extended or adjusted under 35 U.S.C. 154(b) by 638 days.

(21) Appl. No.: 13/158,195

(22) Filed: Jun. 10, 2011

(65) Prior Publication Data

US 2012/0316483 A1    Dec. 13, 2012

(51) Int. Cl.
*A61F 5/00*    (2006.01)

(52) U.S. Cl.
USPC ............................................. 602/19; 128/846

(58) Field of Classification Search
USPC ................. 128/846, 869, 870, 873–876, 868; 602/5, 12, 19, 32, 36, 60, 61, 67; 2/464, 467, 466
See application file for complete search history.

(56) References Cited

U.S. PATENT DOCUMENTS

| 3,663,797 | A | 5/1972 | Marsh |
| 5,306,229 | A | 4/1994 | Brandt et al. |
| 5,344,384 | A | 9/1994 | Ostrow et al. |
| 6,440,094 | B1 | 8/2002 | Maas |
| 6,962,572 | B1* | 11/2005 | Zahiri ............................ 602/19 |
| 7,871,388 | B2 | 1/2011 | Brown |
| 2005/0197607 | A1 | 9/2005 | Brown |
| 2012/0059297 | A1* | 3/2012 | Newkirk ......................... 602/19 |

OTHER PUBLICATIONS

EC3D, "EC3D: Redefining Orthopedic Compression Wear . . . One Stitch at a Time", web pages, www.ec3d.ca, Jun. 9, 2011, Laval, QC, Canada URL: www.ec3d.ca.

* cited by examiner

*Primary Examiner* — Michael A. Brown
(74) *Attorney, Agent, or Firm* — Schiff Hardin LLP

(57) ABSTRACT

High friction scapular retraction straps for application directly to the tops of the respective shoulders of a patient and connected with tension straps to draw the gripper straps and, consequently, the shoulders rearwardly, and including fasteners to fasten to a garment worn by the patient to hold the shoulders rearward.

20 Claims, 6 Drawing Sheets

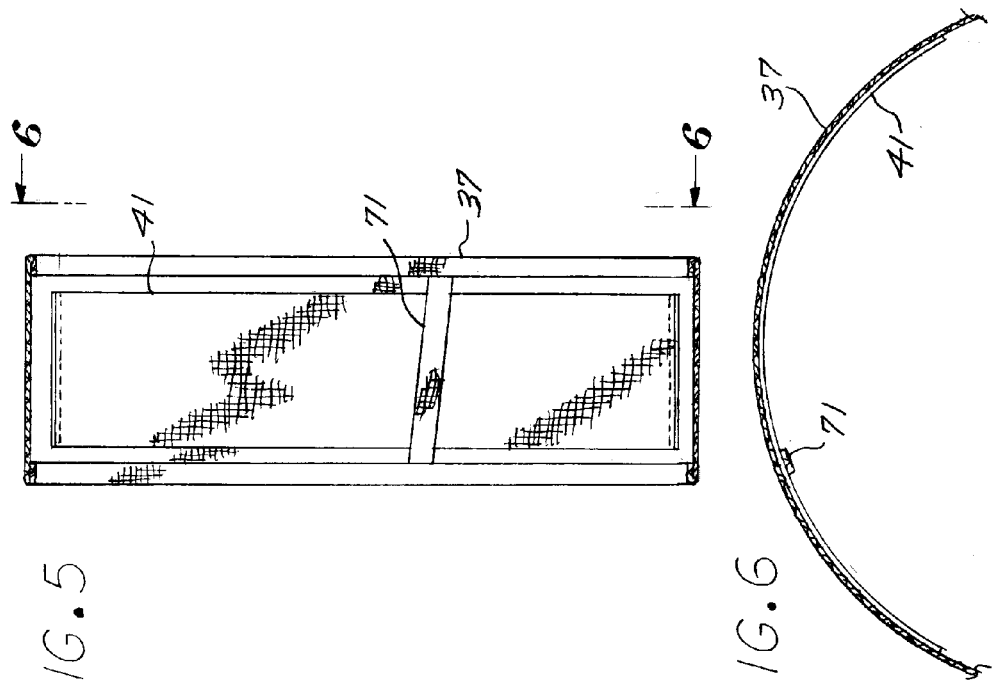
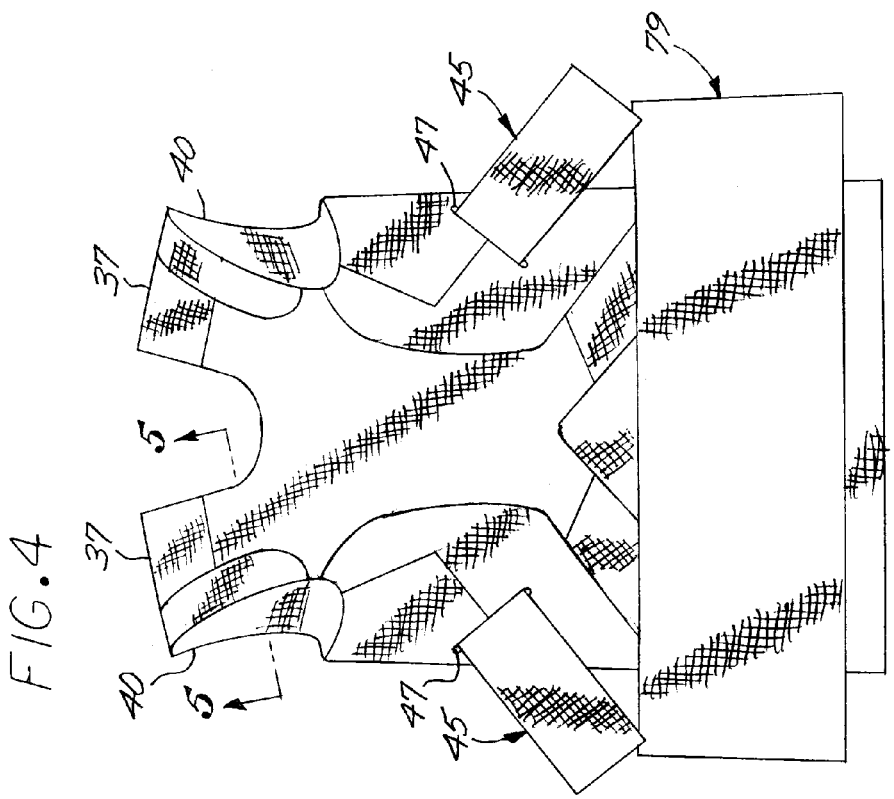

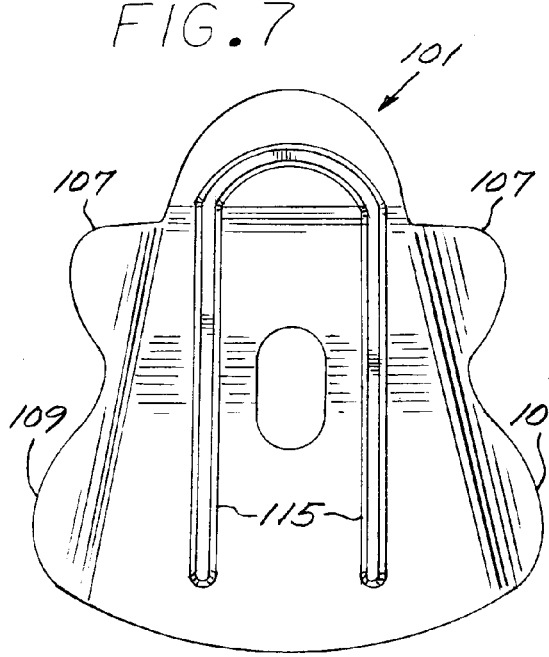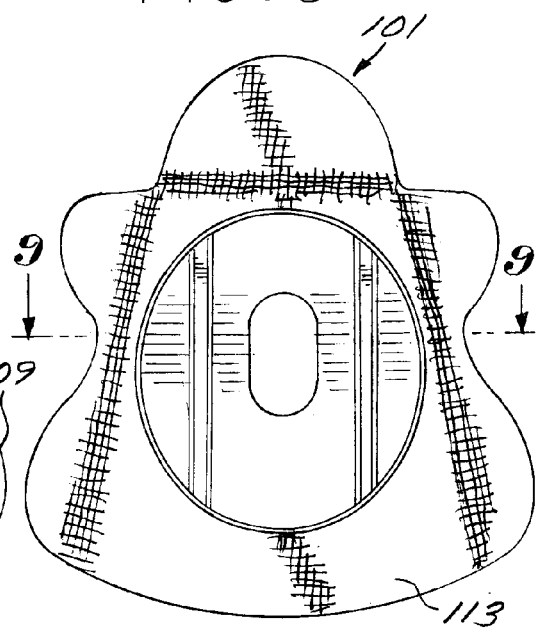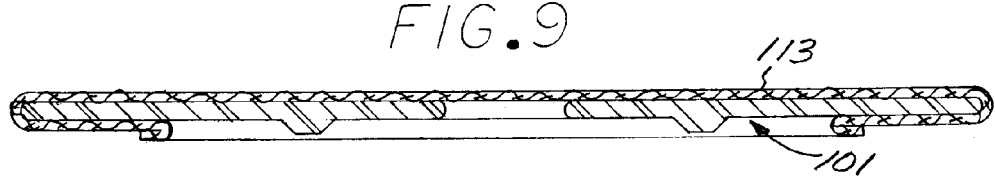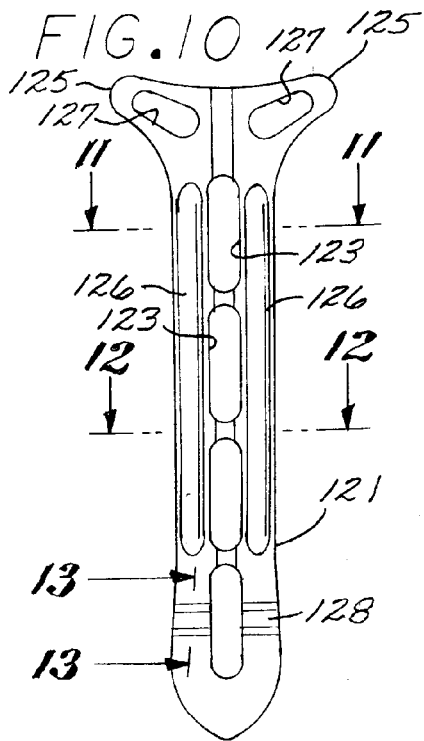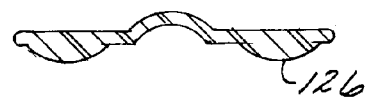

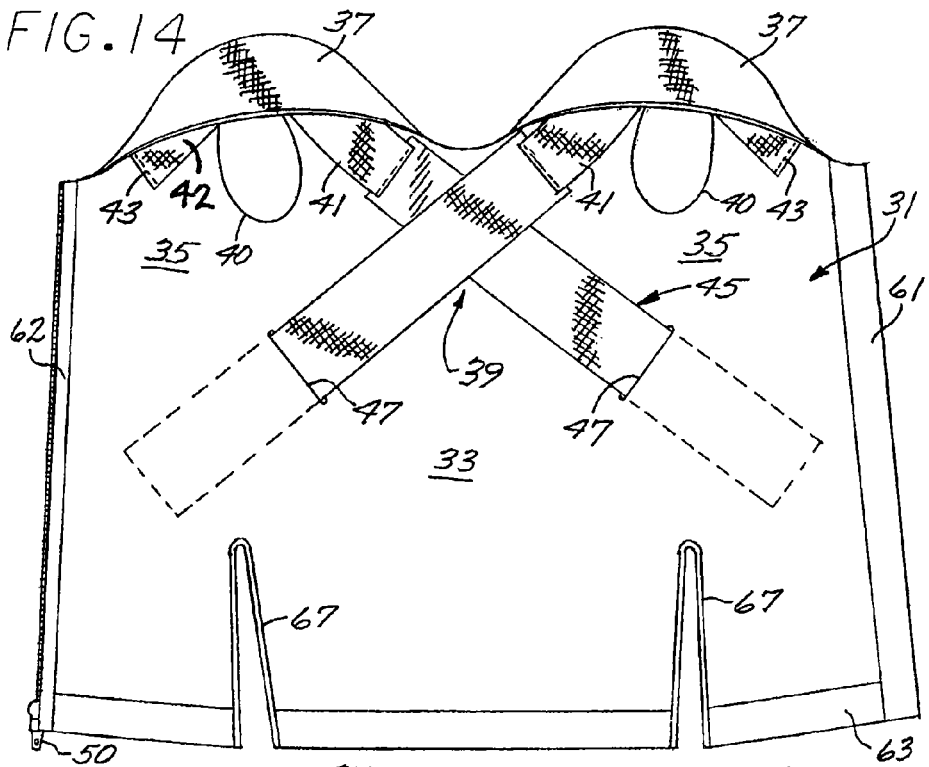
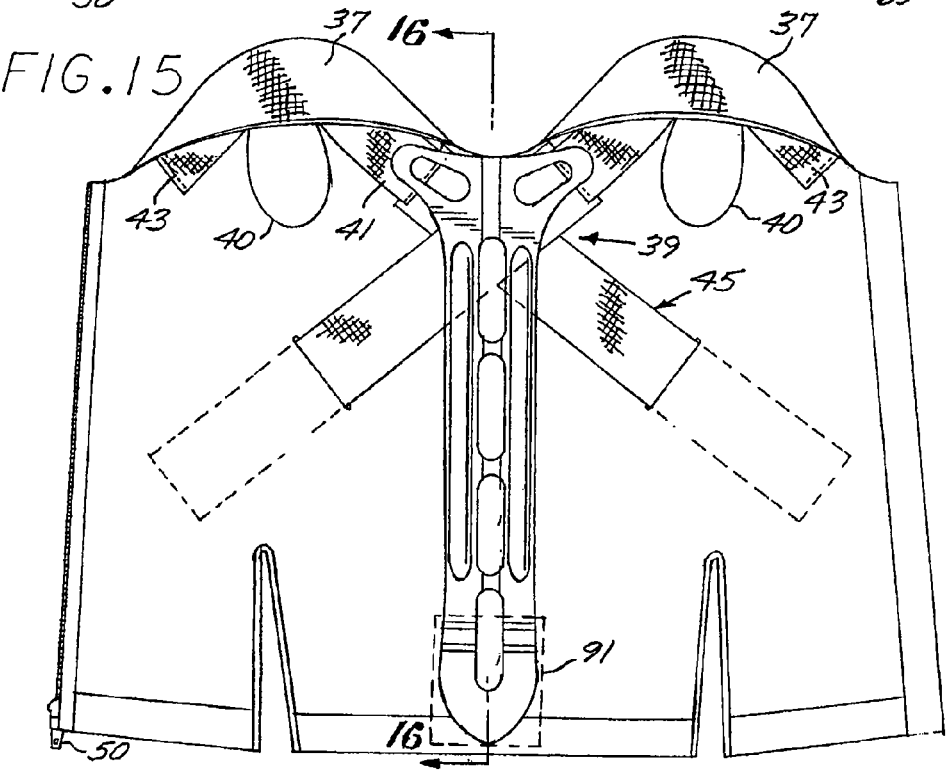

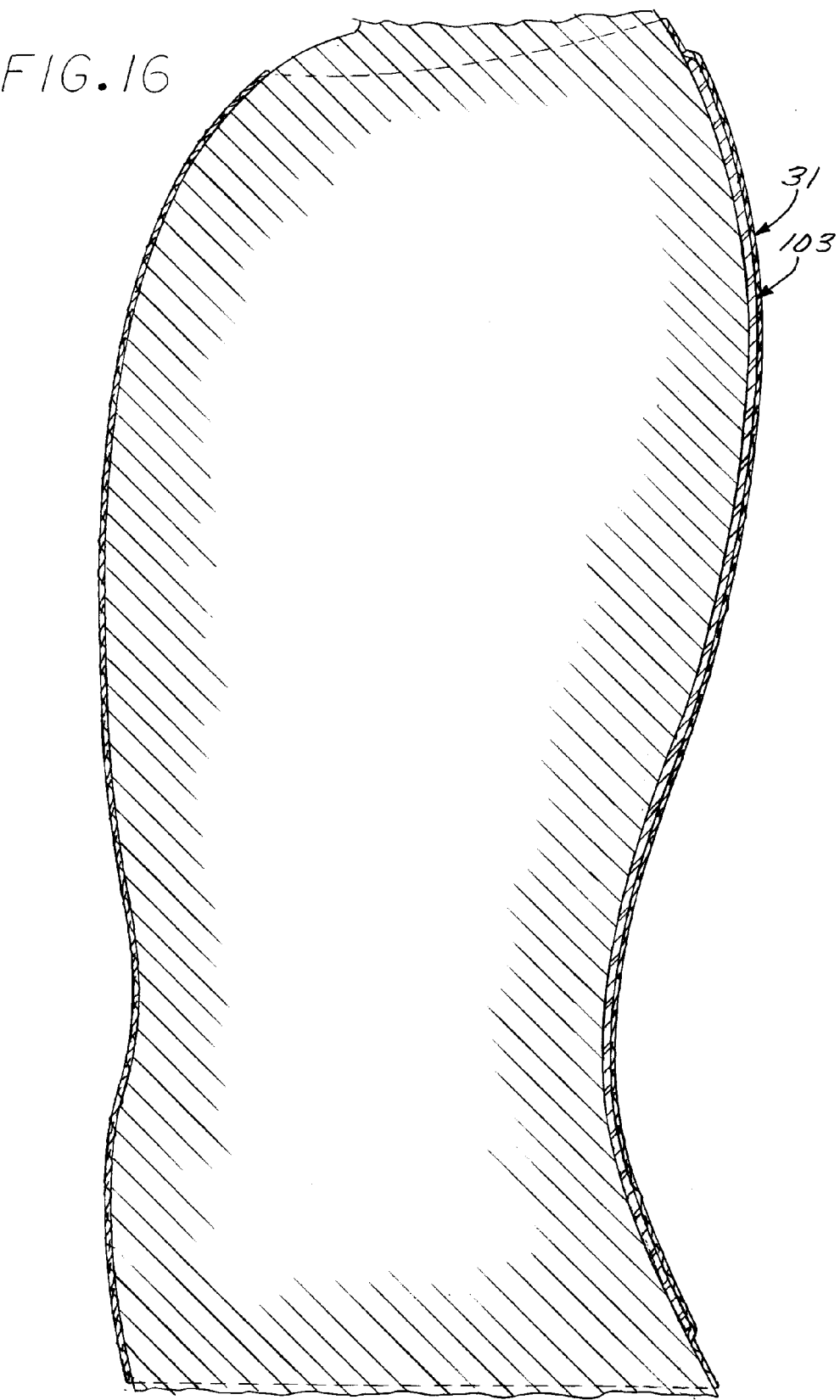

THORACIC LUMBAR SACRAL POSTURE GARMENT DEVICE

BACKGROUND OF THE INVENTION

1. Field of the Invention

The present invention relates to medical orthopedic devices and particularly to braces for improving the posture of a patient to treat medical ailments.

2. Brief Description of Related Art

Medical costs are one of the greatest concerns to various societies throughout the world, including the United States, which is involved in disputes over procedures and laws to be followed in an effort to reduce the tremendous expenses to consumers, taxpayers, the government and insurance companies stemming from various different types of maladies. Additionally, may patients suffering from spinal or structural maladies are forced to endure long term pain and deterioration of the body stemming from various injuries, skeletal deterioration, osteoporosis and the like.

Tasks involved in everyday work compound the problems encountered by patients tending to suffer from the affliction stemming from improper posture. Much of the work performed by various individuals involves addressing work pieces located forward of the body, such as on a desk or the like, as in the case of personal computers, where workers tend to sometimes hunch over, bend the spine forward and oftentimes fold the shoulders forwardly into improper posture positions.

The bones in the thoracic and particularly in the shoulder girdle area, include the clavicle and scapula, which can be generally described as a flat or planar bone of triangular shape, situated back of the rib cage and typically articulated with movement of the arms, oftentimes shifted forwardly and downwardly when the worker concentrates intently on desk work or machining or work activity located forwardly and downwardly from the worker's head or neck. The shoulder joint is a ball-and-socket joint formed by a large globular head of the humerus and the elongated glenoid cavity in the scapula which receives the humeral head. The ligaments of the shoulder encircle the ball-and-socket structure and are often exposed to considerable stress or repetitive movement, all too frequently resulting in irritation and inflammation of the muscles and tendons, even to the point requiring surgery or considerable physical therapy in an effort to overcome the pain and discomfort involved.

The thoracic spine and shoulder are constructed to work in tandem to maintain the patient standing tall and with a pleasing posture. Injury or instability can result in stooping, leading to pain throughout the body from headaches to lower back pain, and general diminishment in the quality of life.

It has been recognized that spinal injury typically stems from imbalance, such as a person's posture slouching forward for extended periods of time, which may cause tight anterior musculature and weak posterior musculature, sometimes even resulting in pectoral muscles in the chest becoming permanently shortened, thus making it difficult of not impossible for the worker to fully straighten his or her back and hold the shoulders back. This imbalance is the cause of numerous different injuries and afflictions, specifically in the neck, shoulder and spine area, oftentimes resulting in the loss of work time sometimes even debilitating the worker to the point where he or she must be assigned different tasks.

Posture changes which occur over time are typically referred to as kyphosis. When the vertebrae fracture, typically in the upper (thoracic) spine, the patient will oftentimes experience pain, height loss, and a stooped or hunched posture.

The spine is made up of numerous small bones called vertebrae. The various regions of the spine from the bottom (sacrum), to the middle (thoracic) to the top (cervical) can be hunched leaving the head and/or shoulders hunched forwardly of the torso to present undesirable posture.

Osteoporosis afflicts some 50% of women over 50 years of age and decreases of the density of the vertebrae of the spine which oftentimes leads to vertebral fractures which can result in severe pain and discomfort in the patient and millions of dollars in medical costs. The available data reveals that spinal fractures and/or compression fractures in the spine occur in some 550,000 cases per year as a result of osteoporosis.

A patient's recovery from surgery or injury can be stimulated by inducing the patient to assume a more appropriate posture. The various types of injuries experienced can include torn rotor cuff, SLAP (Superior Labral from Anterior to Posterior) tear, shoulder instability, sub-acromial decompression, labral tears, and impingement on the nerves or joints. In each instance rehabilitation may benefit from some degree of posture improvement and/or immobilization.

Various types of harnesses have been proposed for improving posture, typically incorporating upper straps extending over the shoulders and lower straps which extend underneath the armpits to partially embrace the shoulders. These devices typically suffer the shortcoming that the straps underneath the arms contribute to the discomfort of the patient wearing the device, thus discouraging use and defeating the effect sought in treatment of the patient's posture In recognition of the benefits that could be experienced from braces and therapeutic devices to induce better posture, it has been proposed to fit the patient with a short-sleeved shirt such as a t-shirt or other garment and provide crossed straps extending over the shoulders, attached to run across the exterior of the t-shirt or garment and attached at the lower extremities to a device on the garment to hopefully draw the shoulders rearwardly. A device of this type is shown in U.S. Pat. No. 6,440,094 to Maas. A similar device but for use with a pad or the like to be held in the center of the back is shown in U.S. Pat. No. 7,871,388 to Brown.

While serving some of the intended purpose, the shortcoming of devices of this type is that the patient typically benefits most from having the upper area of the shoulders drawn rearwardly to maintain the shoulder blade or scapula in more of a vertical plane. It has been discovered that by extending the restraining straps over the outside of the garment and over the top of the shoulders, the effectiveness of holding the shoulders back is compromised, and thus does not provide the desired effectiveness for improving posture and serving to rehabilitate patient's injuries and the like.

SUMMARY OF THE INVENTION

Briefly and in general terms, the present invention is directed to a scapula retaining device including friction straps extending from the pectoral areas at opposite sides where they are anchored to the interior of a garment to extend over the respective shoulders, gripping directly against the tops of the shoulders, to attach to tension straps which pass diagonally across the back and exit the opposite sides of the garment to releasably attach to the exterior of the garment to anchor such tension straps down drawing the tops of the shoulders rearwardly.

The features and advantages of the invention will be more readily understood from the following detailed description which should be read in conjunction with the accompanying drawings.

BRIEF DESCRIPTION OF THE DRAWINGS

FIG. 4 is a back view of the dynamic thoracic lumbar sacral posture garment device shown in FIG. 1;

FIG. 5 is a transverse sectional view, in enlarged scale, taken along the line 5-5 of FIG. 4;

FIG. 6 is a partial side view taken along the line 6-6 of FIG. 5;

FIG. 7 is a back view of the posterior panel shown in FIG. 2;

FIG. 8 is a back view similar to FIG. 7 but showing a modification where the back panel is covered with fabric;

FIG. 9 is a transverse sectional view, in enlarged scale, taken along the line 9-9 of FIG. 8;

FIG. 10 is a front view of the posterior brace shown in FIG. 3;

FIGS. 11, 12 and 13 are transverse sectional views taken along the lines 11-11, 12-12 and 13-13 respectively of FIG. 10;

FIG. 14 is a front view of the garment device shown in FIG. 1 in its open position;

FIG. 15 is a front view similar to FIG. 14 but showing the posterior panel of FIG. 3 disposed in position;

FIG. 16 is a vertical sectional view, in enlarged scale, taken along the line 16-16 of FIG. 15 showing the garment on a patient and with the brace of FIG. 3 disposed in position.

DETAILED DESCRIPTION OF THE PREFERRED EMBODIMENTS

Figure 1:
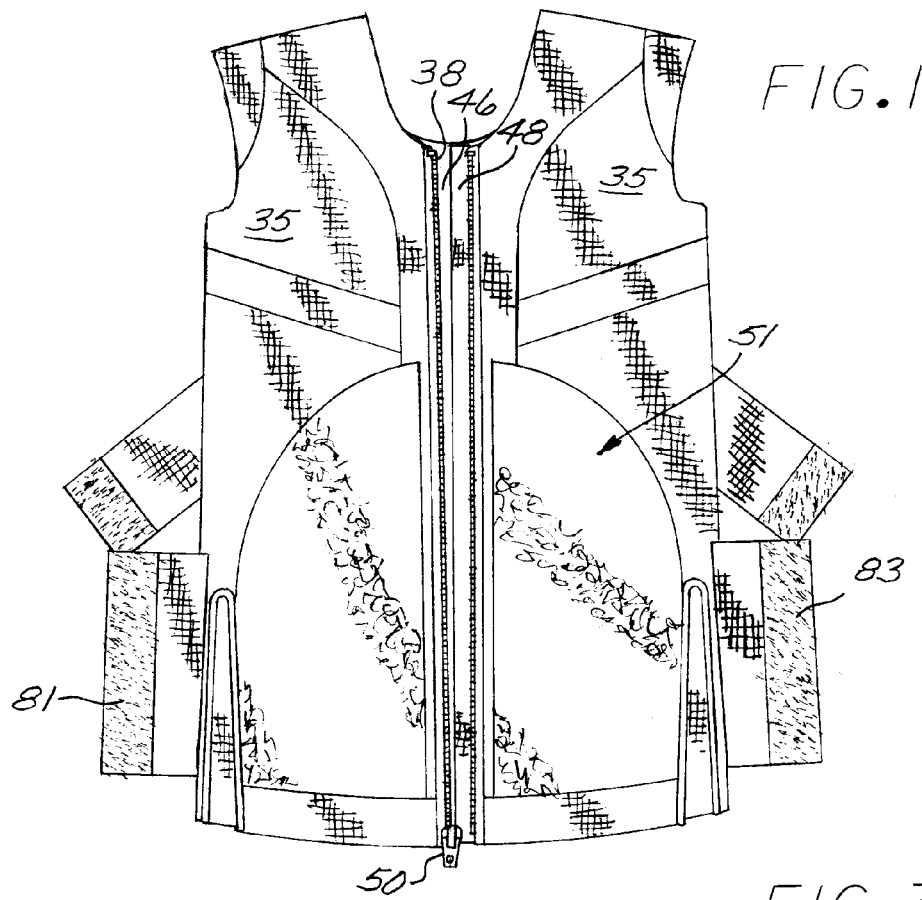
FIG. 1 is a front view of a dynamic thoracic lumbar sacral posture garment device incorporating the present invention.

Referring now in more detail to the exemplary drawings for purposes of illustrating embodiments of the invention, wherein like reference numerals designate corresponding or like elements among the several views, The thoracic lumbar sacral posture garment of the present invention includes, generally, a garment 31 formed with a back panel 33, front panels 35, fastened by a zipper 38, shoulder straps 37, and an interior tensioning device, generally designated 39. The tensioning device includes respective scapular gripping straps 41 anchored to the garment in the pectoral area 43 to pass over the patient's shoulder and be attached to respective tension straps 45 which cross over one another in the back of the patient and pass through respective access slots 47 in the front panels to attach at their respective free extremities to fasteners, jointly designated 51, on the lower portion of the respective front panels.

It is important to alignment of the spine and relief of spine-related and even shoulder-related maladies that the top of the shoulders 59 (FIG. 17) of the patient be drawn rearwardly thereby straightening the scapulas and tending to straighten and unload the spine to thereby maintain the desired posture for facilitating recovery and to minimize further injury stemming from fractures, ligament inflammation, ligament tears and afflictions related to osteoporosis. In this regard, it is an objective of the present invention that the internal tensioning device 39 provide for a gripping action at the top surface of the patient's shoulders 59 and apply rearward forces to the top of the shoulders, to preferably torque the scapulas as the shoulders are drawn rearwardly or posteriorly to maintain the desired posture itself.

To this end, the garment in the preferred embodiment is constructed of stretchable, elastic breathable material capable of applying substantial compression to compression upon being stretched tight on the patient's torso to thereby maintain a firm grip on the patient's waist area to thus provide secure anchoring so that the rearward forces applied by the tensioning device 39 will apply the desired rearward forces to the tops of the patient's shoulders.

In this regard, the garment 31 serves as somewhat of a harness, having a high level of elasticity, but with a great degree of constraint to thereby, when the zipper fastener 38 is fastened, hold the garment relatively tight around the patient's abdomen and waist to thereby form a solid anchor for the tensioning device 39. A material which serves this function quite favorably is a seamless orthopedic compression material with 360 degree stitching with three dimensional compression available from QSD, Lavel, QC, Canada, HZS 2G2.

In construction, the garment includes the usual marginal reinforcing bands 61 and 67 to which the respective zipper sections are connected, and includes a waistband 63 (FIG. 14). Wire eyes 46 are attached in vertically spaced apart relationship on one marginal edge along the zipper and wire hooks 48 attached to the confronting marginal edge for hooking into the respective eyes to hold the garment in closed relationship.

The garment is formed in the lower waist portion with a pair of expandable, downwardly opening, V-shaped vents 67 with which allow for expansion of the waist area to accommodate different waistlines.

The scapula gripping straps 41 of the tensioning device 39 are constructed of high-friction material such as neoprene, silicone, breathoprene, adhesive foam or any other material that has a high friction surface to securely and positively grip the top surfaces of the patient's shoulder to provide for high-friction contact to thereby cooperate in the tension straps pulling forward on the tension straps to thereby draw the top area of the shoulders forwardly, thereby improving the patient's posture. In the preferred embodiment, these straps 41 are inelastic at the level of forces applied of about 25 pounds so as to minimize stretching and relative movement on the surfaces of the shoulders to thus minimize the tendency to break contact, thereby maintaining the grip.

In the preferred embodiment, the tension straps 45 are elastic so that upon application of 10-15 pounds force or more they will stretch to thereby allow for bending and turning of the patient's torso while maintaining the desired tension drawing the back ends of the respective gripper strips 41 rearwardly and downwardly to maintain a firm application of force on the tops of the respective shoulders.

Figure 17:
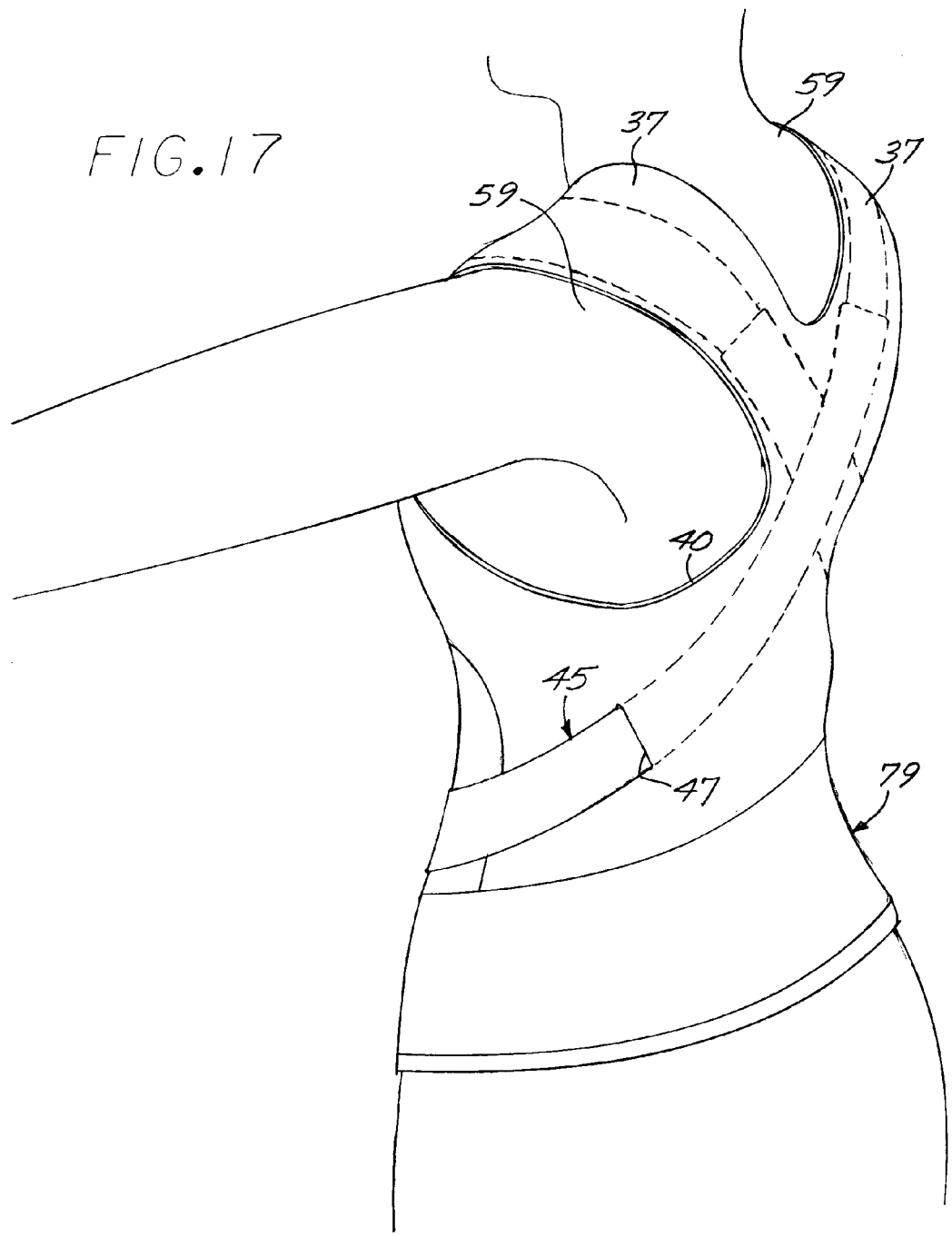
FIG. 17 is a three-quarter rear perspective view of the garment device shown in FIG. 1 worn by a patient.

Referring to FIGS. 14 and 17, it will be noted that the shoulder straps 37 formed with the garment are configured to rest on the tops of the shoulders and preferably incorporate restraining straps 71 (FIG. 5) which constrain the scapula gripping straps 41 (FIG. 5) in position to thus maintain those scapula straps in the most preferential position for applying torque to the tops of the shoulders to draw them rearwardly as tension is applied thereto.

Referring to FIGS. 1 and 4, in the preferred embodiment the garment device includes a waist belt, generally designated 79, which will fit over the lower waist area of the garment and includes on its opposite ends respective fasteners typically in the form of loops and pile 81 and hooks 83 for adjustably fastening the waist band over the lower portion of the garment device to cooperate in holding it downwardly on the torso of the patient.

In practice, the garment is so constructed that its elasticity cooperates in gripping the wearer's waist and torso area, as augmented by the belt 79 when the fasteners 81 and 83 are closed on one another in tight relationship to establish a secure anchor for the lower portion of the garment as the tension straps are tightened. The passage of the tension straps 45 from the interior to the exterior of the garment as dictated by the passage slots 47 is preferably spaced below the armpits, typically in the height of the midriff or thoracic area and is angled and oriented such that the straps themselves will be directed toward the respective fastener panels 51 on the front panels of the garment (FIGS. 1, 14 and 17).

Figure 2:
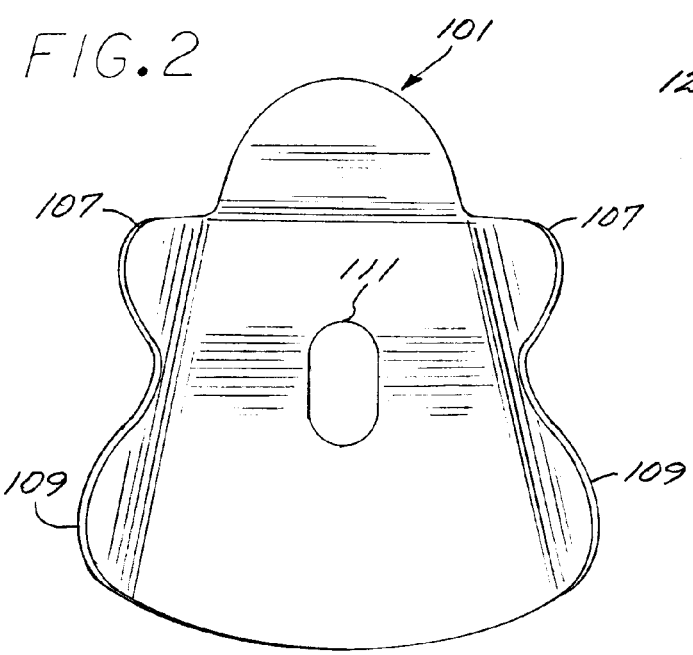
FIG. 2 is a front view of a rigid back brace that may be used with the garment device of FIG. 1.
Figure 3:
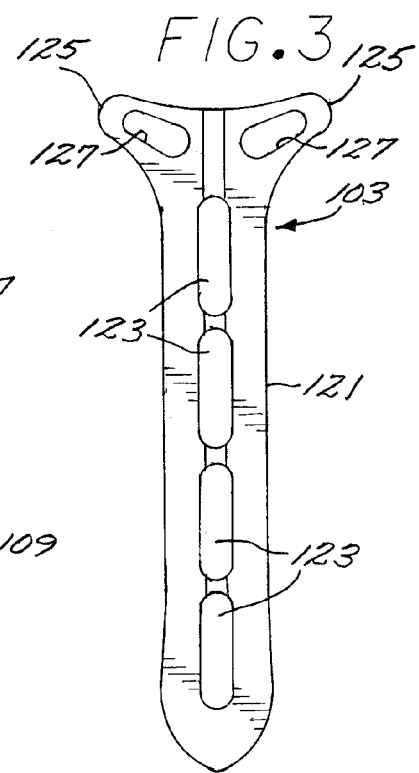
FIG. 3 is a front view of a second embodiment of a rigid back brace that may be employed with the garment device shown in FIG. 1.

Some embodiments of the garment are configured to incorporate a back support plate, generally designated 101, (FIG. 2) or a back support plate stem 103 (FIGS. 3 and 10-13). The back plate 101 may be constructed with a generally forwardly opening structure configured on its opposite sides with outwardly flared upper and lower wings 107 and 109 into which the upper and lower thoracic areas of the wearer's body might nest. In the preferred embodiment, the plate 101 is formed centrally with a ventilation opening 111 and may be covered with a fabric 113 (FIGS. 8 and 9). In one modification, the plate 111 may be formed with a downwardly opening u-shaped reinforcing ribs 115 (FIG. 7).

The stem plate 103 is somewhat t-shaped in a vertical plane and incorporates a stem 121 spaced along its central area with ventilation apertures 123 and configured in its upper extremity with upwardly flared support wings 125 which also include upward and outwardly angled apertures 127.

The bodies of the support plate 101 and stem 103 incorporate hard plastic or may in some instances be constructed of thin aluminum, carbon steel or other relatively rigid materials to lend support to the wearer tending to immobilize the spine and body parts for cooperating with the scapular tension straps to provide support for the wearer and further cooperate in tending to provide somewhat of a pivot point for rotation of the upper portions of the scapulas when the tension straps are tightened and the upper portions of the shoulders drawn rearwardly.

In operation, it will be appreciated that when the garment is to be donned by a wearer, the tab 50 of the zipper fastener 38 will be grasped to unzip the garment to be more or less laid open as shown in FIG. 14. The garment may then be raised to be placed over the wearer's shoulder by inserting the arms through the respective openings 40 under the respective shoulder straps and the scapula gripping straps placed over the shoulders to dispose the respective gripping surfaces 42 in direct contact with the wearer's skin to provide for frictional contact of such surface for high-friction engagement and to provide resistance against rearward sliding of the straps on the surface of the skin. The garment may then be drawn forwardly around wearer's sides so the wearer may engage the hook and eyes 46 and 48 to hold the marginal edges of the garment in close proximity to one another as the wearer or technician grasps the zipper tab 50 to fit the zipper together and draw the garment further together around the patient's thoracic 90, lumbar 92 and sacral 94 of the wearer to thereby apply constraining forces and high friction to the lower portion of the torso, to thereby provide secure anchorage to the torso of the wearer (FIG. 17). The belt 79 may then be wrapped about the waist of the garment and drawn tight to secure the fasteners 81 and 83 (FIG. 1). The wearer or medical technician may then grasp the free ends of the tension straps 45 on the exterior of the garment and draw the tension straps firmly around the thoracic to draw the scapula gripping straps rearwardly to draw the tops of the shoulders rearwardly and, while maintaining the tension, attach the loop and pile fasteners 48 and 52 in tensioning relationship on the respective loop and pile fastener panels 51 to thereby cause the frictional engagement of the scapular straps 41 to maintain the upper portion of the shoulders 59 rearwardly as shown in FIG. 17, thereby pivoting the patient's scapulas rearwardly and enhancing the posture of the patient, and, with fastening of the fasteners on the panels 51, cause the shoulders to be so maintained in favorable posture position.

Then, the patient may go about his or her dynamic daily activities with the shoulders held rearwardly at the upper extremities, free to maneuver his or her chest area about in different directions with the arms free to undertake their daily tasks, all the while secure in the recognition that the top of the shoulders are held rearwardly and constantly reminded of the fact that the shoulder should be so maintained in rearward orientation to thereby provide support for the particular shoulder injury, spine injury or the like being treated so that the improved posture and support will facilitate healing of the particular tears or fractures being treated and restrict forward and downward movement of the shoulders which would otherwise further irritate or aggravate the particular injury.

It will be appreciated that with this particular construction, the top of the shoulders are held rearwardly while leaving the arms free to move about in a normal fashion without restriction by straps and retainers extending underneath the armpits and the like.

This support then tends to facilitate more rapid and full recovery from many types of shoulder injuries, spinal dysfunction and further affords support against stooping posture. By stabilizing the thoracic and lumbar spine, the vertebrae and other structure which may be suffering from injury will heal more rapidly. Holding the tops of the shoulders rearwardly induces muscular activation in a favorable manner, tending to strengthen and shorten the back muscles while extending the pectoral muscles extend to thereby tend towards more favorable posture and support to overcome weak posterior musculature conditions. The support afforded will tend to accelerate rehabilitation of injuries to the rotor cuff labrum and provide support against shoulder instability, relieves discomfort from osteoporosis and will tend to retrain the patient's movement away from postural dysfunction.

For certain types of spinal dysfunction or ailments, it is desirable to incorporate the support and posture positioning of the inventive garment with additional more rigid back support, either along the line of the spine or, in some instances, extending laterally about the back area. For the more extensive support across the lateral back area, a back support panel 101 may be inserted inside the back area of the garment during the application of the garment to the wearer and prior to tightening the tension straps 45. In this regard, in some embodiments, a pocket similar to the pocket 91 for the stem support 105 is provided for nesting of the back support panel 101 in position as the garment is placed on the wearer. Then, as the tension straps are tightened to draw the scapula support straps 41 rearwardly, tension is also applied to the back support panel 101 to provide for stabilization of the spinal area, as well as applying support to the lower portion of the patient's scapulas to thus to maintain the lower portion of the scapulas pressed forwardly and providing a fulcrum for the scapulas as the support straps 41 are drawn rearwardly to thus enhance the tendency of the upper portion of the scapulas to be drawn rearwardly and affording additional support tending to maintain the scapulas in their preferred positions to improve posture. Likewise, the wings 107 on the opposite sides of the support panel tend to hold the thoracic area in a stabilized condition tending to enhance immobilization of the spine and related areas thus enhancing the overall healing effect of the combination.

In other applications, the therapeutic prescription may call for more support in the spine area of the patient, and with less concern for stabilization of the lateral portions of the back, thereby dictating application of the stem brace 103 in a manner similar to that just described for the support panel 101. In those instances, it is possible to merely insert the spine brace 103 within the panel before the tension straps 45 are tightened. In those embodiments where a pocket 91 (FIG. 15) is formed in the interior lower waist area of the garment, the bottom end of the stem may be inserted in that pocket to thus facilitate positioning during application of the garment itself to the patient.

In either the case of the support panel 101 or stem brace 103, it will be appreciated that use of those rigid supports in combination with the garment itself will facilitate immobilization of the various body parts and tend to maintain the shoulders drawn rearwardly and somewhat stabilized, thereby tending to enhance the rate of healing for the particular ailment being treated.

With the foregoing, it will be appreciated that the garment of the present invention provides a particularly effective support for the patient and will enhance the effectiveness of the garment to maintain the top of the shoulders drawn rearwardly to thereby improve posture and potentially accelerate the healing effect stemming from such improved posture and tendency for immobilization.

The invention may be embodied in other forms without departure from the spirit and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention. Accordingly, the scope of the invention is intended to be defined only by reference to the appended claims.

I claim:

1. A dynamic thoracic lumbar sacral posture garment device for improving the posture of a patient and comprising;

an elastic garment for stretching around the thoracic, lumbar and sacral of the patient including back, side and front panels, the front panels including pectoral areas and terminating in adjacent marginal edges, and shoulder straps connected between the back panel and respective side panels to form arm openings;

the back or side panels being formed with respective strap openings spaced below the level of the arm openings;

a garment fastener device attached to at least one of the marginal edges for fastening to the other marginal edge to hold the garment stretched to grip at least the thoracic;

first releasable fasteners mounted on the front surfaces of the respective front side panels;

elongated scapular retraction gripper straps fastened on their respective one ends to the interior of the respective pectoral areas to extend upwardly within the shoulder straps to, when the garment is donned by a patient, project over the respective shoulders of the patient and terminate in respective second ends, the respective straps being formed with downwardly facing high friction surfaces for gripping the patients respective shoulders, and the garment free of straps under the patient's armpits;

an elastic lumbar belt attached to the garment for encircling the area of the patient's lumbar and including belt free ends;

belt fasteners on the free belt ends for releasably fastening the belt free ends together;

elongated tension straps attached on their respective one ends to the respective second ends of the gripper straps and projecting inside the garment diagonally across one another on the inside of the back panel to extend out through the respective strap openings to terminate in respective free tension strap ends configured to overlie the respective first fasteners, the tension straps including respective second fasteners on the respective free ends for adjustably fastening to the respective first fasteners whereby the garment device may be placed on a patient, with the gripper straps over the shoulders and the respective gripper surfaces gripping the shoulders, the tension straps extending across one another in the back to project outwardly through the holes, the front panels drawn together and the garment fastener device fastened to hold the garment stretched to grip at least the thoracic, so that when tension is applied to the free ends of the tension straps to draw down on the respective second ends of the respective gripper straps force will be applied to the high friction surfaces to the respective shoulders to, as the tension forces are applied to the respective second ends, the shoulder straps will tend to draw the tops of the respective shoulders rearward and, while continuing to apply the tension, the second tension strap fasteners may be attached to the first tension strap fasteners.

2. The dynamic thoracic lumbar sacral posture garment device for improving the posture of a patient as set forth in claim 1 wherein:

the scapula gripper straps are constructed of Neoprene.

3. The dynamic thoracic lumbar sacral posture garment device for improving the posture of a patient of claim 1 that includes:

retainers attached to the respective shoulder straps to hold the respective gripper straps in place.

4. The dynamic thoracic lumbar sacral posture garment device for improving the posture of a patient of claim 1 wherein:

the first and second releasable fasteners are constructed of loop and pile material.

5. The dynamic thoracic lumbar sacral posture garment device for improving the posture of a patient of claim 1 wherein:

the garment is constructed to provide, when the front panels are closed by the garment fastener about the patient, provide for three dimensional stretching.

6. The dynamic thoracic lumbar sacral posture garment device for improving the posture of a patient of claim 1 that includes:

an elongated rigid back brace for fitting inside the back panel and wherein;

the garment includes a pocket on the inside of the back panel for receipt of one extremity of the back brace.

7. The dynamic thoracic lumbar sacral posture garment device for improving the posture of a patient of claim 1 wherein:

the gripper straps are inelastic; and the tension straps are elastic.

8. A dynamic thoracic lumbar sacral posture garment device for improving the posture of a patient and comprising:
an elastic garment for surrounding the thoracic, lumbar and sacral of the patient, including pectoral areas and terminating at the front side in marginal edges;
the garment including strap access slots on the opposite sides thereof at a location disposed in the thoracic or sacral area of the garment when donned by a patient;
a garment fastener device attached to one of the marginal edges for fastening to the other of the marginal edges to hold the garment stretched about at least the thoracic of the patient;
elongated scapula gripping straps attached to the interior of the garment in the pectoral areas and configured to, when the device is donned by a patient, extend upwardly and rearwardly over the shoulders of the patient and terminating in respective free ends;
a pair of elongated tension straps attached to the free ends of the scapula gripping straps, extending diagonally on across each other on the interior of the back of the garment and projecting guidingly through the access slots to be formed with respective free ends disposed, when the garment is worn by the patient, on the opposite sides at the front of the garment;
first releasable fasteners on the respective free ends
second fasteners on the opposite front sides of the garment for adjustably fastening to the respective first releasable fasteners.

9. An orthopedic method for dynamically improving the posture of a patient including:
applying an elastic garment to the patient extending around the thoracic pectoral, lumbar and sacral areas of the patient, the garment including high friction scapula retractor gripper straps anchored on their respective one ends to the garment at the respective pectoral areas;
applying the scapular retraction gripper strap in direct contact with at least the tops of the patient's respective shoulders;
applying tension to the respective gripper straps on the respective one sides of the patient to maintain tension, crossing the tension straps on the back of the patient and drawing the respective gripper straps rearwardly on the respective sides to maintain the tops of the respective shoulders drawn rearwardly to hold the upper extremities of the patient's shoulders rearwardly.

10. The orthopedic method for dynamically improving the posture of a patient of claim 9 that includes:
fastening the tension straps to the garment to maintain the tension straps in tension.

11. A dynamic thoracic lumbar sacral posture garment device for improving the posture of a patient and comprising:
elongated gripper strap devices extending for, when the garment is donned by a wearer, extending from the pectoral areas of the wearer, over the tops of the wearer's shoulders and downwardly and inwardly across the wearer's back to cross over one another and terminate at the respective opposite sides of the wearers torso, the gripper strap devices including gripper straps having high friction elements on the underside of the straps extending over the tops of the shoulders;
an elastic garment for fitting over the wearers torso to be held frictionally in place on the torso and having a front panel;
the gripper strap devices being anchored to the interior of the garment in the respective pectoral areas; and
fasteners on the opposite sides of the garment in the waist area for releasably connecting with the respective free ends of the gripper strap devices.

12. The dynamic thoracic lumbar sacral posture garment device of claim 11 wherein:
the garment includes through access slots disposed on the outsides thereof for passage of the respective free ends of the gripper strap devices;
and the fastener elements are disposed on the exterior of the garment.

13. The dynamic thoracic lumbar sacral posture garment device of claim 11 that includes:
a lumbar belt for encircling the area of the patients lumbar to facilitate holding the garment down on the torso.

14. The dynamic thoracic lumbar sacral posture garment device set forth in claim 11 wherein:
the garment is constructed to, when donned, press the gripper straps tightly down on the respective shoulders.

15. The dynamic thoracic lumbar sacral posture garment device set forth in claim 11 wherein:
the garment includes shoulder straps for fitting over the gripper straps on the tops of the shoulder of the wearer; and
retainer straps for looping around the gripper strap devices to hold the respective gripper straps in place.

16. The dynamic thoracic lumbar sacral posture garment device of claim 11 wherein:
the gripper straps are constructed of elastic; and
the garment device includes inelastic tension straps extending across the patient's back and terminating in the respective free ends.

17. The dynamic thoracic lumbar sacral posture garment device of claim 11 wherein:
the garment is constructed of a seamless orthopedic compression material with 360° stitching constructed for 3-dimensional compression to, when donned by the wearer, provide for close fit about the wearer's torso and over the wearer's shoulders.

18. A method of holding the tops of a wearer's shoulders drawn rearwardly including:
selecting a pair of elongated gripper strap devices formed on the underside with high friction gripping material to be positioned directly on the wearer's shoulders, the strap devices selected of a length to extend from the respective pectoral areas of the wearer up and rearwardly over the opposite shoulder to project downwardly and inwardly across the wearers back to cross over one another;
placing the strap devices on the wearer to project from the respective pectoral area rearwardly over the tops of the shoulders and then downwardly across the wearer's back to terminate in respective free ends;
placing an elastic garment on the wearer over the respective gripper straps to tightly fit about the wearers shoulders and torso to press the gripper straps in position;
drawing the free ends of the respective gripper strap devices downwardly to cause such strap devices in the area of the tops of the shoulders to be drawn rearwardly thereby drawing the tops of the respective shoulders rearwardly; and
fastening the free ends of the gripper strap devices to the garment to maintain the respective shoulders and associated scapulae drawn rearwardly.

19. The method of claim 18 that includes:
fastening a belt around the lumbar area of the wearer to hold the bottom extremity of the garment frictionally downwardly on the wearer's torso.

20. The method of claim 18 that includes:
projecting the free ends of the gripper strap devices through slots in the opposite sides of the garment and fastening the free ends to the exterior of the garment.

* * * * *